US010213578B2

(12) United States Patent
Fukuoka et al.

(10) Patent No.: US 10,213,578 B2
(45) Date of Patent: Feb. 26, 2019

(54) CATHETER ASSEMBLY

(71) Applicant: TERUMO KABUSHIKI KAISHA, Shibuya-ku, Tokyo (JP)

(72) Inventors: Tetsuya Fukuoka, Fujinomiya (JP); Yuya Otake, Fujinomiya (JP); Kouta Hamuro, Fujinomiya (JP); Koichiro Tashiro, Fujinomiya (JP); Mariko Maruyama, Fujinomiya (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 786 days.

(21) Appl. No.: 14/661,121

(22) Filed: Mar. 18, 2015

(65) Prior Publication Data
US 2015/0265802 A1 Sep. 24, 2015

(30) Foreign Application Priority Data
Mar. 20, 2014 (JP) .................. 2014-057485

(51) Int. Cl.
*A61M 25/00* (2006.01)
*A61M 25/06* (2006.01)
(Continued)

(52) U.S. Cl.
CPC ........ *A61M 25/0021* (2013.01); *A61M 25/00* (2013.01); *A61M 25/0041* (2013.01);
(Continued)

(58) Field of Classification Search
CPC ...... A61M 2025/0681; A61M 25/0041; A61M 2025/0059; A61M 2025/0006;
(Continued)

(56) References Cited

U.S. PATENT DOCUMENTS

| 4,636,346 A | * | 1/1987 | Gold ............... A61M 25/001 138/109 |
| 5,447,503 A | * | 9/1995 | Miller ............. A61M 25/0068 604/528 |

(Continued)

FOREIGN PATENT DOCUMENTS

JP 2004-357805 A 12/2004

*Primary Examiner* — Nathan R Price
*Assistant Examiner* — Anh Bui
(74) *Attorney, Agent, or Firm* — Buchanan Ingersoll & Rooney PC

(57) ABSTRACT

A catheter assembly includes an outer catheter and an inner catheter. The inner catheter has an accommodation unit which can be positioned on a farther distal side than an outer catheter body in a state where an inner catheter body is inserted into the outer catheter body, extends in a proximal direction from the inner catheter body, and can accommodate an outer catheter distal portion so as to surround an outer circumference thereof in a state where the outer catheter distal portion formed at a distal end of the outer catheter body is reduced in diameter. The outer catheter distal portion can be separated from the accommodation unit and can expand in diameter by moving the inner catheter body in a distal end direction relatively with respect to the outer catheter body from a state of being accommodated in the accommodation unit.

12 Claims, 19 Drawing Sheets

(51) Int. Cl.
*A61M 25/10* (2013.01)
*A61M 25/01* (2006.01)

(52) U.S. Cl.
CPC .... *A61M 25/0069* (2013.01); *A61M 25/0074* (2013.01); *A61M 25/0102* (2013.01); *A61M 2025/0004* (2013.01); *A61M 2025/0006* (2013.01); *A61M 2025/0024* (2013.01); *A61M 2025/0025* (2013.01); *A61M 2025/0059* (2013.01); *A61M 2025/0081* (2013.01); *A61M 2025/0175* (2013.01); *A61M 2025/0183* (2013.01); *A61M 2025/0681* (2013.01); *A61M 2025/1013* (2013.01); *A61M 2210/12* (2013.01)

(58) Field of Classification Search
CPC .. A61M 2025/0025; A61M 2025/0183; A61M 2025/1013; A61M 2210/12; A61M 2025/0175; A61M 2025/0004; A61M 2025/0024; A61M 25/00; A61M 25/0021
USPC ....... 604/95.03, 158, 164.01, 264, 508, 523, 604/525, 532, 533
See application file for complete search history.

(56) References Cited

U.S. PATENT DOCUMENTS

| | | | | |
|---|---|---|---|---|
| 5,674,240 A * | 10/1997 | Bonutti | ............. | A61B 17/0401 604/264 |
| 6,436,119 B1 * | 8/2002 | Erb | .................... | A61B 17/3417 606/185 |
| 7,993,351 B2 * | 8/2011 | Worley | ............. | A61M 25/0041 600/585 |
| 8,636,728 B2 * | 1/2014 | Watson | .................. | A61B 18/02 606/191 |
| 9,114,227 B2 * | 8/2015 | Blanchard | .......... | A61B 17/3415 |
| 2004/0019359 A1 * | 1/2004 | Worley | ............. | A61M 25/0041 606/129 |
| 2005/0015007 A1 | 1/2005 | Itou et al. | | |
| 2006/0212022 A1 * | 9/2006 | Gellman | ........... | A61M 25/0097 604/509 |
| 2008/0167610 A1 * | 7/2008 | Dann | ................. | A61M 25/0119 604/104 |
| 2008/0195141 A1 * | 8/2008 | Teague | .................. | A61M 25/10 606/200 |
| 2009/0221965 A1 * | 9/2009 | Osypka | ............. | A61M 25/0662 604/160 |
| 2009/0299261 A1 * | 12/2009 | Bognar | ............. | A61M 25/0045 604/6.16 |
| 2011/0144572 A1 * | 6/2011 | Kassab | ............. | A61M 25/0084 604/35 |
| 2015/0126931 A1 * | 5/2015 | Holm | ................ | A61M 25/0618 604/164.08 |
| 2015/0246211 A1 * | 9/2015 | Bunch | .................. | A61M 29/02 128/200.26 |
| 2016/0310701 A1 * | 10/2016 | Pai | ..................... | A61M 25/0138 |

* cited by examiner

CATHETER ASSEMBLY

CROSS-REFERENCES TO RELATED APPLICATIONS

This application claims priority to Japanese Application No. 2014-057485 filed on Mar. 20, 2014, the entire content of which is incorporated herein by reference.

TECHNICAL FIELD

The present invention relates to a catheter assembly in which a shaft is inserted into a lumen of an outer catheter.

BACKGROUND DISCUSSION

Recently, a method has been adopted for medical treatment and diagnoses which is carried out through a lumen formed inside a catheter after the catheter is inserted into a biological lumen such as a blood vessel so as to reach a target site. Generally, a catheter includes a long tubular catheter body and a catheter hub which is interlocked with a proximal portion of a catheter body. Catheter bodies have been decreased in thickness so as to maximize the inner diameter in order to secure a wide space in a lumen. Catheter development has progressed to the point that catheters can be inserted into a blood vessel narrower than the femoral artery such as the radial artery. A decreased outer diameter necessary for a catheter body to be inserted into a narrow blood vessel also promotes reduction in thickness of the catheter body.

A decreased thickness of a catheter body may result in collapse and kinking (bending) of the catheter body due to degraded strength thereof, and thus, it may be difficult for the catheter body to pass through a bent blood vessel. Moreover, due to an occurrence of collapse and a kink, it is difficult for a medical instrument or liquid such as medicine and a contrast agent to pass through the inside of a lumen. As the strength of a catheter body is degraded, it is difficult for the catheter body to be thrust forward in a blood vessel due to a degraded pushing performance (pushability) thereof. In addition, the decreased thickness of a catheter body causes a distal portion of the catheter body to be sharp, and thus, biological tissue is easily damaged.

In order to decrease an occurrence of collapse and a kink while decreasing the thickness of a catheter body, a method has been proposed in which a catheter (an inner catheter) or a dilator is inserted into another catheter (an outer catheter) (for example, refer to Japanese Application Publication No. 2004-357805). As a shaft such as an inner catheter is inserted into an outer catheter, appropriate stiffness can be applied by the shaft while decreasing the thickness of the outer catheter. Thus, an occurrence of collapse and a kink can be suppressed when the catheter is inserted into a blood vessel, and a pushing performance can also be improved.

SUMMARY

However, in a case of a double catheter, a step difference is formed by a distal portion of an outer catheter with respect to an outer surface of a shaft. Therefore, if the distal portion of the outer catheter is thin in thickness, there is a possibility that the thin and sharp distal portion of the outer catheter comes into contact with biological tissue, thereby causing damage to the biological tissue. If the distal portion of the outer catheter is thick in thickness, when a double catheter configured to have an outer catheter and an inner catheter is inserted into a blood vessel, there is a possibility that the distal portion of the outer catheter is caught in biological tissue so as to be turned inside out. In this case, there is a possibility that the distal portion of the outer catheter increases resistance of the double catheter when being inserted into a blood vessel and causes damage to biological tissue.

The catheter assembly disclosed here aims to provide a catheter assembly in which a shaft is movably arranged inside an outer catheter and loads to biological tissue applied by a distal portion of the outer catheter can be reduced.

The catheter assembly disclosed here includes an outer catheter comprised of a tubular outer catheter body, with the outer catheter body possessing a distal end portion terminating at a distal-most end of the outer catheter body; and a shaft comprised of a shaft body insertable into the outer catheter body. The shaft includes an accommodation unit extending in a proximal direction from the shaft body, positionable distal of the distal-most end of the outer catheter body in a state where the shaft body is positioned in the outer catheter body, and configured to accommodate the distal end portion of the outer catheter body so that the accommodation unit surrounds the outer circumferential surface of the distal end portion of the outer catheter body and an outer diameter of the distal end portion of the outer catheter body is decreased relative to the outer diameter of the distal end portion of the outer catheter body before the distal end portion of the outer catheter body is accommodated in the accommodation unit. The distal end portion of the outer catheter body is separable from the accommodation unit by relatively moving the shaft body in a distal end direction with respect to the outer catheter body from the state of being accommodated in the accommodation unit so that the outer diameter of the distal end portion of the outer catheter body expands upon being separated from the accommodation space.

In a catheter assembly having the above-described configuration, an accommodation unit is formed in a shaft so as to be able to accommodate the distal end portion of the outer catheter in a state of being decreased in diameter. Therefore, the outer catheter distal portion can be accommodated in the accommodation unit and can move inside a biological lumen without being exposed outside, and thus, loads to biological tissue can be reduced. The outer catheter distal portion can be separated from the accommodation unit and can expand in diameter by moving a shaft body in a distal end direction relatively with respect to an outer catheter body from a state of being accommodated in the accommodation unit. Therefore, the inner space of the outer catheter body can be widened due to the expanded diameter of the outer catheter body, and thus, the shaft body can be arranged to be movable inside the outer catheter body.

The distal end portion of the outer catheter can have a thickness in a radial direction thicker than that of a proximal portion of the outer catheter body, and so the distal end portion of the outer catheter can be prevented from being sharp as much as possible, and thus, damage to biological tissue can be minimized.

The minimum inner diameter of the outer catheter distal portion in a state where the outer catheter distal portion is separated from the accommodation unit and expands in diameter can coincide with the outer catheter distal end portion in an axial line direction or to be equal to or greater than the maximum outer diameter of a portion of the shaft which can be positioned on distally beyond the outer catheter distal portion, and so a portion which needs to pass through the inside of the outer catheter distal portion can rather easily passes through the inside of the outer catheter distal portion.

The outer catheter distal end portion is accommodated in the accommodation unit, and so if at least one of an outer side accommodation surface of the accommodation unit facing an outer circumferential surface of the outer catheter distal end portion and inner side accommodation surface of the outer catheter body facing an inner circumferential surface of the outer catheter distal end portion is caused to be annularly formed while being flexural in waves on a cross section which is orthogonal to an axial line of the shaft body, the outer catheter distal end portion can be accommodated in the accommodation unit while effectively maintaining a state of being flexural in waves and being decreased in diameter.

The distal end portion of the outer catheter partially includes fragile portions which are relatively low in rigidity and are formed in a circumferential direction, the outer catheter distal end portion is rather easily bent at the fragile portions, and thus, the outer catheter distal portion can be more easily decreased in diameter.

The outer catheter distal portion is accommodated in the accommodation unit in a state of being decreased in outer diameter, and so a user can omit a process to accommodate the outer catheter distal end portion in the accommodation unit, and thus, workability is improved.

Another aspect of the disclosure here involves a catheter assembly positionable in a blood vessel of a living body and comprising: an outer catheter configured to be positioned in the blood vessel in the living body and comprising a tubular outer catheter body possessing a distal end portion terminating at a distal-most end of the outer catheter body; and a shaft comprised of a tubular shaft body open at opposite ends and possessing a distal-most end and a proximal-most end. The shaft includes an accommodation unit positioned so that a portion of the shaft body extends distally beyond a distal-most end of the accommodation unit and a portion of the shaft body extends proximally beyond a proximal-most end of the accommodation unit, with the accommodation unit extending in a proximal direction from the shaft body in axial overlying and spaced apart relation to an outer circumferential surface of a portion of the shaft body so that a gap exists between the accommodation unit and the portion of the shaft body defining an accommodation space that is configured to receive the distal end portion of the outer catheter body. The shaft is configured to be positioned in the outer catheter, with the shaft and the outer catheter being relatively movable such that the shaft and the outer catheter body are positionable in a first state in which the distal end portion of the shaft body is positioned in the accommodation space with the accommodation unit overlying and contacting the distal end portion of the shaft body to reduce the outer diameter of the distal end portion of the shaft body and are positionable in a second state in which the distal end portion of the shaft body is removed from the accommodation space to expand the outer diameter of the distal end portion of the shaft body.

According to another aspect, a method comprises: introducing a shaft and an outer catheter into a blood vessel in a living body, wherein the shaft is positioned inside the outer catheter, and the shaft comprises a tubular shaft body and an accommodation unit positioned so that a portion of the shaft body extends distally beyond a distal-most end of the accommodation unit and a portion of the shaft body extends proximally beyond a proximal-most end of the accommodation unit, with the accommodation unit extending in a proximal direction from the shaft body in axial overlying and spaced apart relation to an outer circumferential surface of a portion of the shaft body so that a gap exists between the accommodation unit and the portion of the shaft body defining an accommodation space, and wherein the outer catheter comprises a tubular outer catheter body possessing a distal end portion positioned in the accommodation space. The shaft and the outer catheter are introduced into the blood vessel in the living body while the distal end portion of the outer catheter is positioned in the accommodation space. The method also includes moving the shaft and the outer catheter along the blood vessel in the living body while the distal end portion of the outer catheter remains positioned in the accommodation space, relatively moving the shaft and the outer catheter to remove the distal end portion of the outer catheter from the accommodation space while the shaft and the outer catheter remain positioned in the living body, and removing the shaft from the living body while the outer catheter remains in the living body.

DETAILED DESCRIPTION

Hereinafter, embodiments of the catheter assembly representing examples of the catheter assembly disclosed here will be described with reference to the drawings. For convenience of description, dimensional ratios of the drawings may be exaggerated and so the illustrated dimensional ratios may be different from the actual dimensional ratios. In the descriptions below, a grip side of a catheter assembly is referred to as "a proximal side" or "a proximal end", and a side to be inserted into a living body is referred to as "a distal side" or "a distal end".

Figure 1:
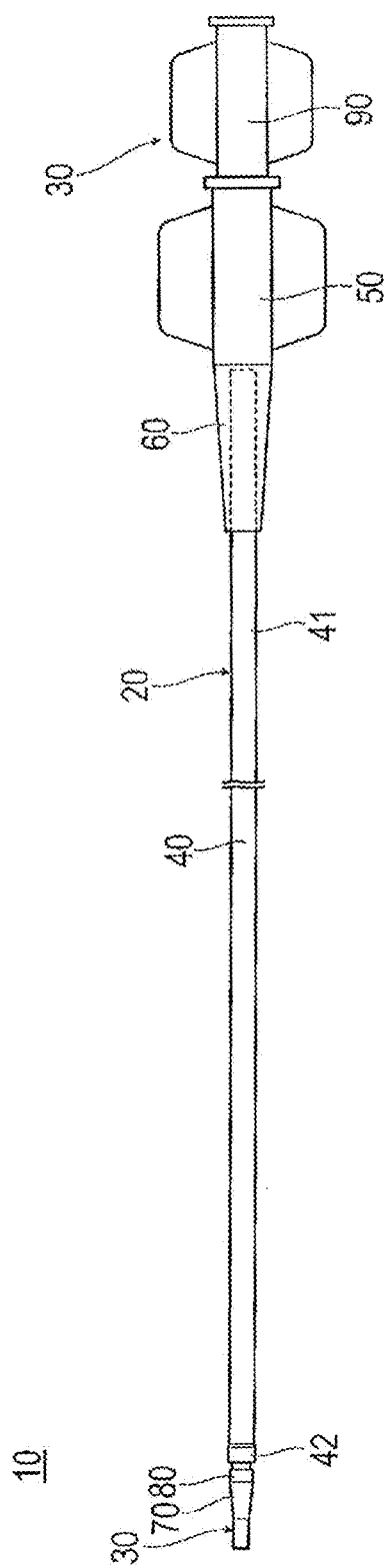
FIG. 1 is a plan view illustrating a catheter assembly according to one embodiment disclosed by way of example.
Figure 2:
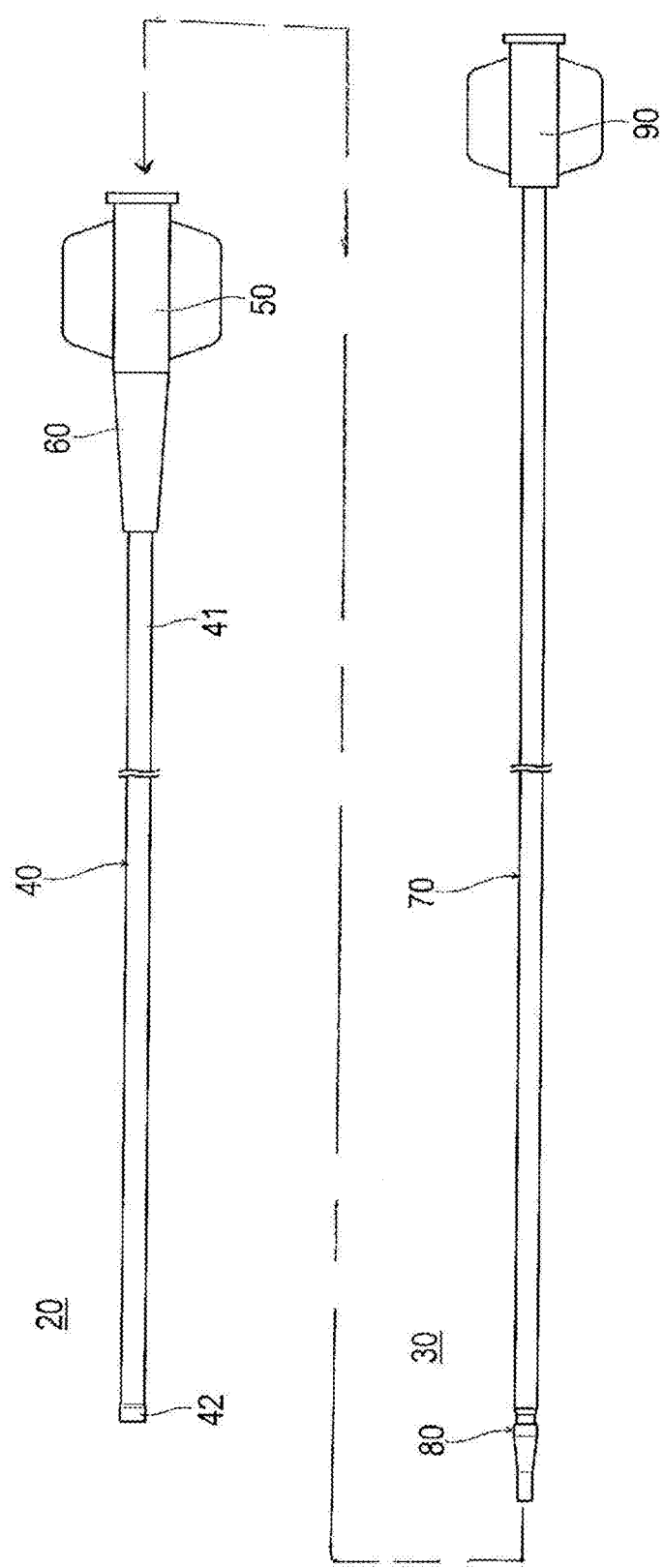
FIG. 2 is a plan view illustrating an outer catheter and an inner catheter.

As illustrated in FIGS. 1 and 2, a catheter assembly 10 according to an embodiment representing one example of the catheter assembly disclosed here is configured to have a double structure including an outer catheter 20 and an inner catheter 30 (a shaft). The catheter assembly 10 is used to be inserted percutaneously into the radial artery, the brachial artery, the femoral artery, and the like so as to cause a distal end of the catheter assembly to reach a target site through a blood vessel. Thus, a treatment catheter such as a balloon catheter, as well as various types of liquid such as a contrast agent, a drug solution, and saline are introduced to a target site.

The outer catheter 20 includes a tubular outer catheter body 40, an outer hub 50 which is mounted on a proximal end of the outer catheter body 40, and a kink resistant protector 60.

The inner catheter 30 includes a tubular inner catheter body 70 (a shaft body) which is insertable into the outer catheter body 40, an accommodation unit 80 which extends in a proximal direction from a distal portion of the inner catheter body 70, and an inner hub 90 which is mounted on a proximal end of the inner catheter body 70.

In an assembled state of the outer catheter 20 and the inner catheter 30, a distal end of the inner catheter body 70 is inserted into a proximal end of the outer hub 50 so as to cause the outer hub 50 and the inner hub 90 to come into contact with each other as illustrated in FIG. 1. It is preferable that the catheter assembly 10 is provided with lock means which holds the inner hub 90 and the outer hub 50 in an interlocked state in which the inner and outer hubs are interlocked with each other. In this case, a state where a distal end of the inner catheter body 70 is inserted into the proximal end of the outer hub 50, and the outer hub 50 and the inner hub 90 are interlocked with each other, is a state of the catheter assembly in which the outer catheter 20 and the inner catheter 30 are assembled. In the assembled state of the catheter assembly, the distal end of the outer catheter body 40 is accommodated in an accommodation unit 80 of the inner catheter. Lock means may be formed by providing a spiral groove on an inner circumferential surface of the inner hub 90 so as to fit a flange of the outer hub 50. Such a configuration fixes the outer catheter 20 and the inner catheter 30 to each other so that the inner and outer catheter 30, 20 do not relatively rotate and move, and thus, a practitioner can rather easily operate the catheter assembly.

Figure 3:
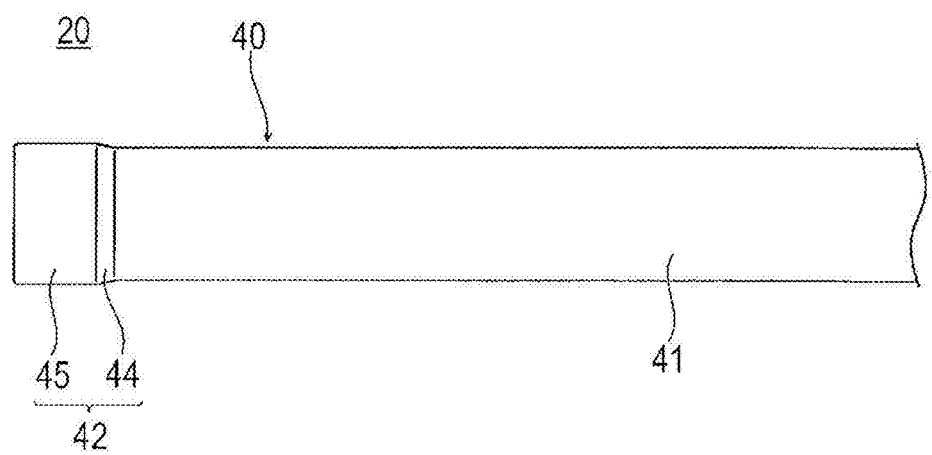
FIG. 3 is a plan view illustrating a distal portion of the outer catheter.
Figure 4:
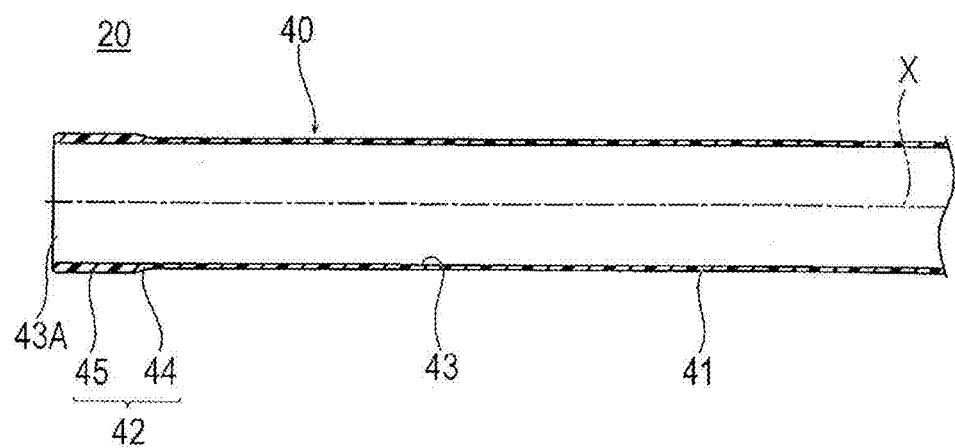
FIG. 4 is a longitudinal cross-sectional view illustrating the distal portion of the outer catheter.

Firstly, the outer catheter 20 will be described. As illustrated in FIGS. 2 to 4, the outer catheter body 40 is configured as a tubular body having flexibility.

The outer catheter body 40 includes an outer catheter proximal portion 41 which extends in a distal end direction from the outer hub 50 in a substantially linear manner. The outer catheter body 40 also includes a tip 42 which is fixedly attached to a distal end of the outer catheter proximal portion 41 and is formed of a material softer than that of the outer catheter proximal portion 41 so as to be able to be easily deformed.

A lumen 43 is formed in a substantially middle (i.e., the central portion as seen in a transverse cross-section) of the outer catheter body 40 throughout the overall length of the outer catheter body 40. The lumen 43 is open at a distal end of the tip 42, thereby forming an outer catheter distal end opening portion 43A.

The tip 42 includes a tapered portion 44 which is fixed to the distal end of the outer catheter proximal portion 41 and which possesses an outer diameter expanding toward the distal end direction in a tapered manner. The tip 42 also includes an outer catheter distal portion 45 which extends in the distal end direction from the distal end of the tapered portion 44.

The tip or distal end portion of the outer catheter body 42 can be deformed so as to be decreased in diameter toward the middle (center) in a radial direction. In a state where no external force is applied to the tip 42 resulting in no deformation (hereinafter, referred to as "a natural state"), the outer diameter of the outer catheter distal portion 45 is substantially uniform along an axial line (center axis) X of the outer catheter body 40 and is greater than the outer diameter of the outer catheter proximal portion 41. In a natural state, the inner diameter of the outer catheter distal portion 45 is substantially uniform along the axial line X and is equal to or greater than the maximum outer diameter of a portion which can pass through the inside of the outer catheter distal portion 45 in an axial line X direction of the inner catheter 30. Here, the portion which can pass through the inside of the outer catheter distal portion 45 denotes or refers to a portion which coincides with the outer catheter distal portion 45 in the axial line X direction and a portion which can be positioned on a farther distal side than the outer catheter distal portion 45, in the inner catheter 30.

The tip 42 is formed of a flexible material softer than that of the outer catheter proximal portion 41. Accordingly, when the assembled catheter assembly 10 is inserted into a living body, damage to a blood vessel caused by the distal end of the outer catheter body 40 can be further suppressed.

The outer diameter of the outer catheter distal portion 45 is not particularly limited. However, in consideration of the narrowed diameter of the outer catheter body 40, it is preferable to be normally equal to or less than 3 mm, more preferable to be equal to or less than 2.5 mm, and further preferable to be equal to or less than 2.0 mm. The outer diameter of the outer catheter proximal portion 41 is not particularly limited. However, it is preferable to be smaller than the outer diameter of the outer catheter distal portion 45 and to have a difference therebetween is less than 0.3 mm (i.e., the difference between the outer diameter of the outer catheter proximal portion 41 and the outer diameter of the outer catheter distal portion 45 is less than 0.3 mm).

It is preferable for the thickness of the outer catheter distal portion 45 to be normally equal to or less than 0.25 mm, more preferable to be equal to or less than 0.20 mm, and further preferable to be equal to or less than 0.17 mm. It is preferable for the thickness of the outer catheter proximal portion 41 to be thinner than that of the outer catheter distal portion 45 and is normally equal to or less than 0.15 mm, more preferable to be equal to or less than 0.12 mm, and further preferable to be equal to or less than 0.10 mm.

The length of the outer catheter body 40 can be appropriately set depending on usage of the outer catheter 20 within a range of 500 mm to 2,500 mm, for example.

As a material for configuring the outer catheter proximal portion 41, for example, there are various thermo-plastic elastomers such as styrene-based, polyolefin-based, polyurethane-based, polyester-based, polyamide-based, polybutadiene-based, trans-polyisoprene-based, fluororubber-based, and chlorinated polyethylene-based. Moreover, a combination (a polymer alloy, a polymer blend, a laminated body, and the like) including two or more types among thereof can be exemplified. A coiled reinforcement member or a braided reinforcement member that is formed by weaving multiple wire rods may be embedded in the outer catheter proximal portion 41. The material forming the reinforcement member is not particularly limited. However, an example of a material is a metallic member such as stainless steel and a nickel-titanium alloy.

The material forming the tip 42, various rubber materials can be exemplified such as natural rubber, isoprene rubber, butadiene rubber, chloroprene rubber, silicone rubber, fluorine rubber, and styrene-butadiene rubber, as well as various thermoplastic elastomers such as styrene-based, polyolefin-based, polyurethane-based, polyester-based, polyamide-based, polybutadiene-based, trans-polyisoprene-based, fluororubber-based, and chlorinated polyethylene-based.

In the outer catheter 20, at least a portion which comes into contact with the inner catheter body 70 when the inner catheter body 70 is inserted into the lumen 43 may be formed of a low friction material. As a low friction material, various resin materials can be exemplified such as polyolefin, polyamide, polyether polyamide, polyester polyamide, polyester, polyurethane, soft polyvinyl chloride, an ABS resin, an AS resin, and a fluorine-based resin such as polytetrafluoroethylene.

Since insertion of the catheter assembly 10 into a living body is performed while checking positions of catheter assembly 10 under X-ray fluoroscopy, it is preferable to compound a radiopaque material (an X-ray contrast agent) in a configuration material of the outer catheter body 40. As a radiopaque material, barium sulfate, bismuth oxide, and tungsten can be used, for example. Such a radiopaque material may be partially present in the outer catheter body 40, without being limited to a case of being present throughout the overall length of the outer catheter body 40. That is, the radiopaque material can be present in only a portion of the outer catheter body 40 and need not be present throughout the outer catheter body 40.

The outer hub 50 is mounted on (fixed to) the proximal end of the outer catheter body 40. A passage for communicating with the lumen 43 of the outer catheter body 40 is formed inside the outer hub 50. The passage is open at the proximal end.

Through the outer hub 50, for example, long instruments (linear objects) such as a guide wire, catheters (for example, a PTCA balloon catheter), an endoscope, an ultrasonic probe, and a temperature sensor can be inserted or removed, or various types of liquid such as a contrast agent (an X-ray contrast agent), a drug solution, and saline can be injected or discharged. For example, the outer hub 50 can connect with other instruments when measuring a blood pressure.

The kink resistant protector 60 is attached so as to cover a portion where the outer catheter body 40 and the outer hub 50 are interlocked with each other, thereby playing a role to help prevent an occurrence of a kink of the outer catheter 20 in the interlocked portion.

The inner catheter 30 will now be described. As illustrated in FIGS. 2 and 5 to 8, the inner catheter body 70 includes an inner catheter proximal portion 71 which extends in the distal end direction from the inner hub 90 in a substantially linear manner, a first inner catheter decreasing diameter portion 72 which extends in the distal end direction from a distal end of the inner catheter proximal portion 71, an inner catheter smaller diameter portion (inner catheter relatively small diameter portion) 73 which extends in the distal end direction from a distal end of the first inner catheter decreasing diameter portion 72, a second inner catheter decreasing diameter portion 74 which extends in the distal end direction from a distal end of the inner catheter smaller diameter portion 73, and an inner catheter distal portion 75 which extends in the distal end direction from the second inner catheter decreasing diameter portion 74.

A lumen 76 is formed in a substantially middle portion (i.e., the central portion as seen in a transverse cross-section) of the inner catheter body 70 throughout the overall length of the inner catheter body 70. The lumen 76 is open at a distal end of the inner catheter distal portion 75, thereby forming an inner catheter distal end opening portion 76A.

The outer diameter of the first inner catheter decreasing diameter portion 72 decreases in the distal end direction from the distal end of the inner catheter proximal portion 71 in a tapered manner. The outer diameter of the proximal end of the first inner catheter decreasing diameter portion 72 coincides with (i.e. merges directly into) the outer diameter of the distal end of the inner catheter proximal portion 71, and the outer diameter of the distal end of the first inner catheter decreasing diameter portion 72 coincides with (i.e. merges directly into) the outer diameter of the proximal end of the inner catheter small diameter portion 73.

Figure 5:
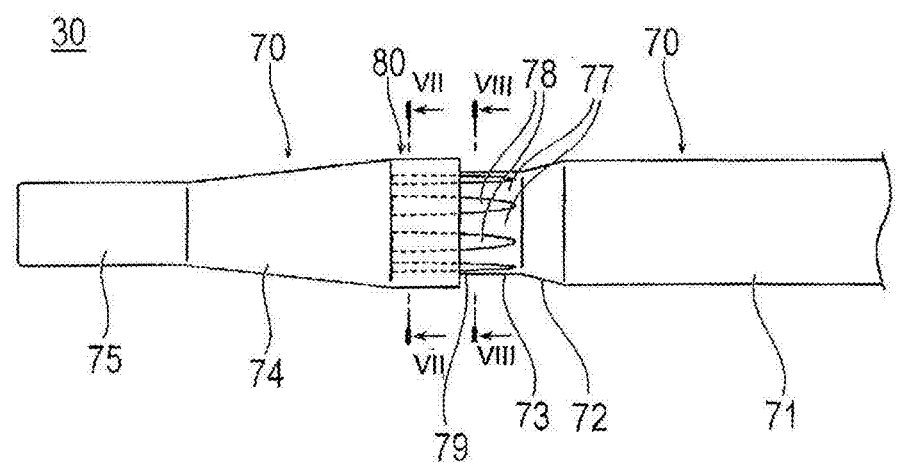
FIG. 5 is a plan view illustrating a distal portion of the inner catheter.
Figure 7:
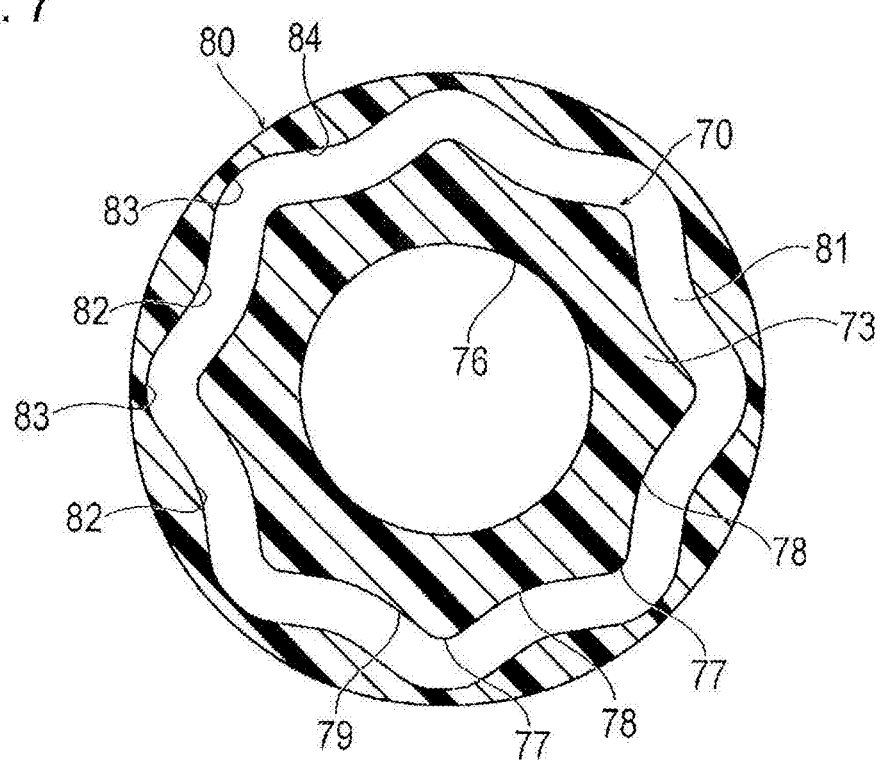
FIG. 7 is a transverse cross-sectional view taken along the section line VII-VII in FIG. 5.
Figure 8:
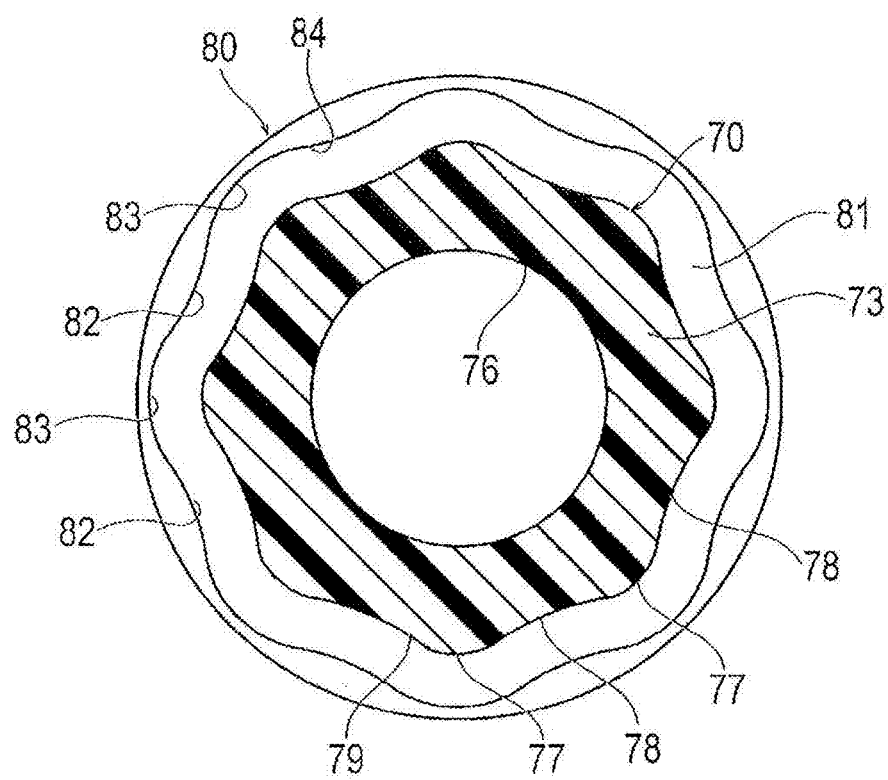
FIG. 8 is a transverse cross-sectional view taken along the section line VIII-VIII in FIG. 5.

The inner catheter smaller diameter portion 73 extends in the distal end direction from the distal end of the first inner catheter decreasing diameter portion 72, and the outer diameter of the inner catheter smaller diameter portion 73 is decreases in the distal end direction in a tapered manner. The outer diameter of the inner catheter smaller diameter portion 73 is smaller than the outer diameter of the inner catheter proximal portion 71. As illustrated in FIGS. 5, 7, and 8, inner convex portions 77 and inner concave portions 78 are alternately arranged in a circumferential direction on an inner side accommodation surface 79 which is formed on the outer circumferential surface of the inner catheter smaller diameter portion 73. The inner side accommodation surface 79 is annularly formed (possesses an annular shape) while being flexural in a wavy-shaped manner on a cross section which is orthogonal to an axial line (center axis) Y of the inner catheter 30. That is, the outer surface of the inner catheter smaller diameter portion (i.e., the inner side accommodation surface 79) is wavy-shaped as seen in transverse cross-section, and this wavy shape of the inner side accommodation surface 79 deforms the outer catheter distal portion 45 in an undulating manner (i.e., in a manner that generally follows the wavy or undulating configuration of the inner side accommodation surface 79) when the outer catheter distal portion 45 is positioned in the accommodation unit 80. This deformation of the outer catheter distal portion 45 decreases the outer diameter of the outer catheter distal portion 45 uniformly and effectively. The outer catheter distal portion 45 can be rather easily and elasticity deformed by accommodating the outer catheter distal portion 45 in the gap or accommodation space between the inner side accommodation surface 79 and the outer side accommodation surface 84 (i.e., in the accommodation unit 80) since the outer catheter distal portion 45 is formed of a relatively soft material. The height of the inner convex portion 77 gradually increases in the distal end direction, and the depth of the inner concave portion 78 gradually deepens in the distal end direction. Eight inner convex portions 77 and eight inner concave portions 78 are provided in the embodiment. However, the number is not particularly limited.

Figure 6:
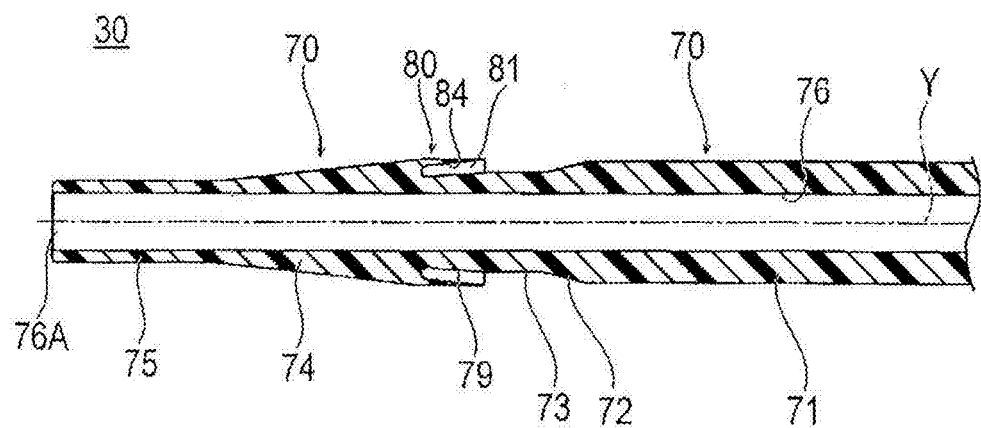
FIG. 6 is a longitudinal cross-sectional view illustrating the distal portion of the inner catheter.

As illustrated in FIGS. 5 and 6, the outer diameter of the second inner catheter decreasing diameter portion 74 decreases in the distal end direction from the distal end of the inner catheter smaller diameter portion 73. The outer diameter of the proximal end of the second inner catheter decreasing diameter portion 74 is substantially the same as the outer diameter of the inner catheter proximal portion 71, and the outer diameter of the distal end of the second inner catheter decreasing diameter portion 74 coincides with (merges directly into) the outer diameter of the proximal end of the inner catheter distal portion 75.

The inner catheter distal portion 75 extends in the distal end direction from the distal end of the second inner catheter decreasing diameter portion 74, and the outer diameter of the inner catheter distal portion 75 is substantially the same as the outer diameter of the distal end of the second inner catheter decreasing diameter portion 74 along the axial line Y. The inner catheter distal portion 75 forms a terminal portion of the inner catheter 30. At least the distal end of the inner catheter distal portion 75 may be formed of a flexible material softer than other portions on the proximal side. Accordingly, when the assembled catheter assembly 10 is inserted into a living body, damage to a blood vessel caused by the distal end of the inner catheter body 70 can be suppressed. Examples of the material forming the inner catheter distal portion 75 are the same as the material described above for the tip 42.

The accommodation unit 80 is formed integrally with the inner catheter body 70 and extends in the proximal direction from the second inner catheter decreasing diameter portion 74. The accommodation unit is spaced proximally from the distal-most end of the inner catheter body 70 and is spaced distally from the proximal-most end of the inner catheter body 70. Also, as shown in FIG. 6, the accommodation unit 80 is positioned so that a portion of the inner catheter body 70 extends distally beyond a distal-most end of the accommodation unit 80 and a portion of the inner catheter body 70 extends proximally beyond a proximal-most end of the accommodation unit 80. The accommodation unit 80 surrounds the outer surface of the inner catheter smaller diameter portion 73, axially overlaps the inner catheter smaller diameter portion 73 and forms an accommodation space 81 which is a gap with respect to the outer circumferential surface of the inner catheter small diameter portion 73. As illustrated in FIGS. 7 and 8, outer convex portions 82 and outer concave portions 83 are alternately arranged in the circumferential direction on an outer side accommodation surface 84 which is formed on an inner circumferential surface of the accommodation unit 80. The outer side accommodation surface 84 is annularly formed (possesses an annular shape) while being flexural in a wavy-shaped manner on a cross section which is orthogonal to the axial line (center axis) Y of the inner catheter 30. That is, the inner surface of the accommodation unit 80 (i.e., the outer side accommodation surface 84) is wavy-shaped as seen in transverse cross-section, and this wavy shape of the outer side accommodation surface 84 deforms the outer catheter distal portion 45 in an undulating manner (i.e., in a manner that generally follows the wavy or undulating configuration of the outer side accommodation surface 84) when the outer catheter distal portion 45 is positioned in the accommodation unit 80. This deformation of the outer catheter distal portion 45 decreases the outer diameter of the outer catheter distal portion 45 relatively uniformly and effectively. The outer catheter distal portion 45 can be rather easily and elasticity deformed by accommodating the outer catheter distal portion 45 in the gap or accommodation space between the inner side accommodation surface 79 and the outer side accommodation surface 84 (i.e., in the accommodation unit 80) since the outer catheter distal portion 45 is formed of a relatively soft material. The outer convex portion 82 is arranged at a circumferential position facing the inner concave portion 78, and the outer concave portion 83 is arranged at a circumferential position facing the inner convex portion 77. The height of the outer convex portion 82 gradually increases in the distal end direction, and the depth of the outer concave portion 83 gradually deepens in the distal end direction. A gap between the inner side accommodation surface 79 and the outer side accommodation surface 84 substantially coincides with (i.e., is substantially equal to) the thickness of the outer catheter distal portion 45, and it is preferable to be normally equal to or less than 0.3 mm, more preferable to be equal to or less than 0.25 mm, and further preferable to be equal to or less than 0.2 mm. Eight outer convex portions 82 and eight outer concave portions 83 are provided in the embodiment. However, the number is not particularly limited. The length of the accommodation unit 80 in a direction along the axial line Y is not particularly limited. However, it is preferable to be normally equal to or less than 10 mm, more preferable to be equal to or less than 5 mm, and further preferable to be equal to or less than 2 mm. The accommodation unit 80 can be easily formed by laser processing, for example.

Figure 14:
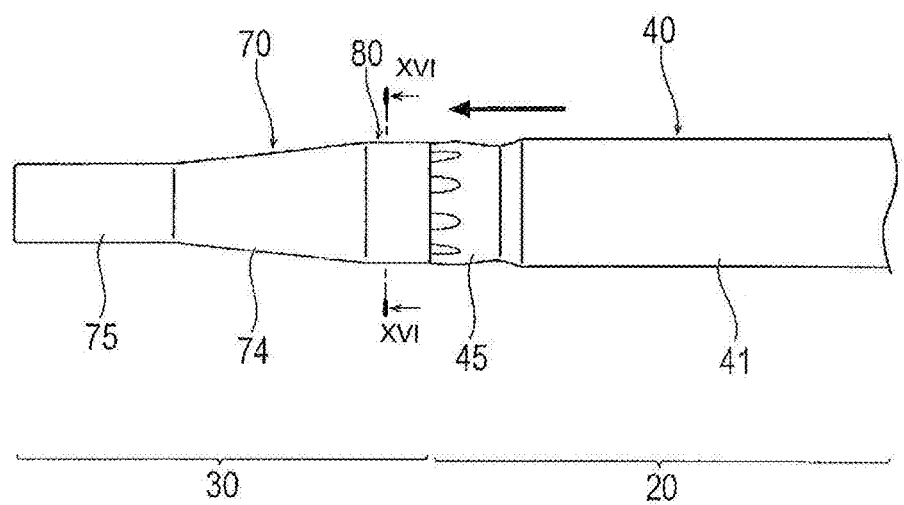
FIG. 14 is a plan view illustrating a state where the outer catheter distal portion is accommodated in an accommodation unit.
Figure 15:
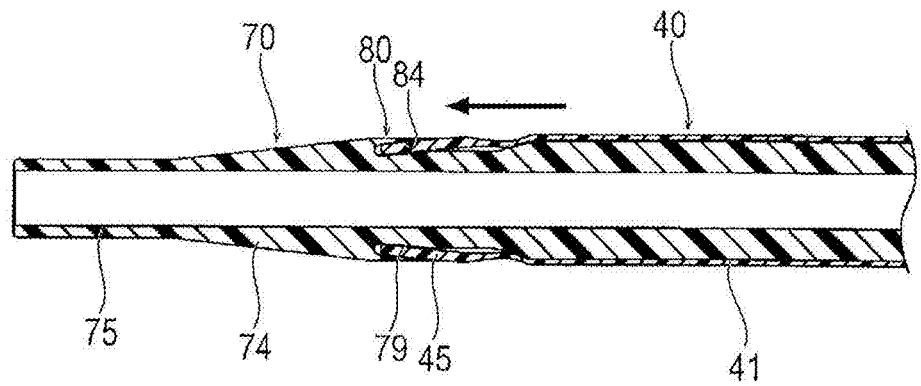
FIG. 15 is a longitudinal cross-sectional view illustrating the state where the outer catheter distal portion is accommodated in the accommodation unit.
Figure 16:
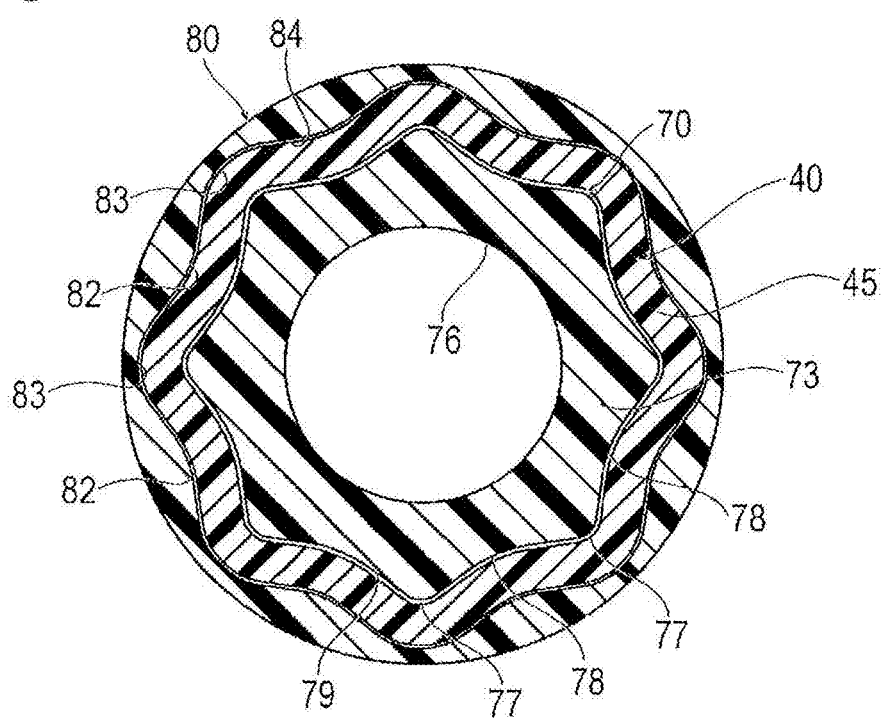
FIG. 16 is a transverse cross-sectional view taken along line XVI-XVI in FIG. 14.

As illustrated in FIGS. 14 to 16, the accommodation unit 80 can accommodate the outer catheter distal portion 45 while surrounding an outer circumference of the outer catheter distal portion 45 which is deformed along the outer side accommodation surface 84 and the inner side accommodation surface 79 and is decreased in inner and outer diameter.

The outer diameters of the inner catheter proximal portion 71 and the accommodation unit 80 are sized so as to allow the lumen 43 of the outer catheter body 40 to pass through (i.e., the inner catheter proximal portion 71 and the accommodation unit 80 can be positioned in the lumen 43 of the outer catheter body 40) The ratio of the outer diameter of the inner catheter proximal portion 71 to the inner diameter of the outer catheter body 40, and the ratio of the outer diameter of the accommodation unit 80 to the inner diameter of the outer catheter body 40 preferably ranges from 0.9 to 0.99. However, the ratio is not limited thereto. The inner diameter of the inner catheter body 70 is set to a size of 0.4 mm to 1.4 mm, for example, so that a guide wire can be inserted into the body. However, the size is not limited thereto.

The length of the inner catheter body 70 is slightly longer than that of the outer catheter body 40, for example, within a range of 800 mm to 3,000 mm. However, the length is not limited thereto.

As a material for configuring the inner catheter body 70, various resin materials can be exemplified, that is, polyamide, polyether polyamide, polyester polyamide; polyester such as polyethylene terephthalate, and polybutylene terephthalate; polyurethane; polyvinyl chloride; an ABS resin; an AS resin; a fluorine-based resin such as polytetrafluoroethylene; a polyester elastomer; a polyurethane elastomer; and polyolefin. A coiled reinforcement member or a braided reinforcement member that is formed by weaving multiple wire rods may be embedded in the inner catheter body 70. A material of the reinforcement member is not particularly limited. However, an example of a material is a metallic member such as stainless steel and a nickel-titanium alloy.

The inner hub 90 is mounted on (fixed to) the proximal end of the inner catheter body 70. A passage for communicating with the lumen 76 of the inner catheter body 70 is formed inside the inner hub 90. The passage is open at the proximal end.

Through the inner hub 90, a guide wire can be inserted and removed. Through the inner hub 90, long instruments (linear objects) such as catheters (for example, a PTCA balloon catheter), an endoscope, an ultrasonic probe, and a temperature sensor may be insertable or removable, or various types of liquid such as a contrast agent (an X-ray contrast agent), a drug solution, and saline may be able to be injected or discharged.

Set forth next is a description regarding an assistive device 100 for accommodating the outer catheter distal portion 45 in the accommodation unit 80 of the inner catheter 30.

Figure 9:
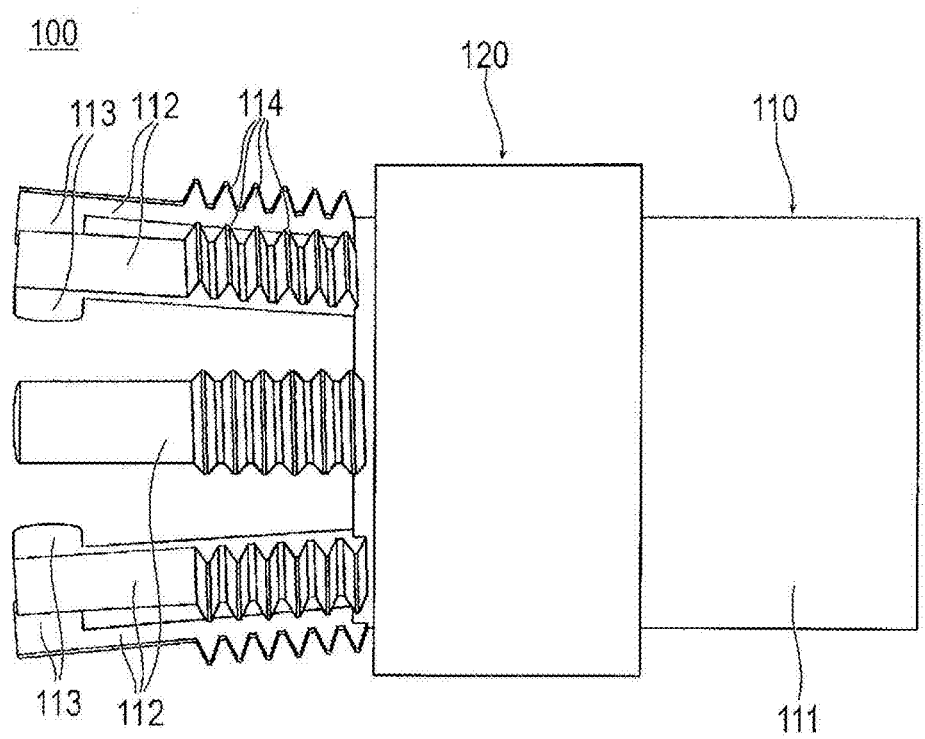
FIG. 9 is a plan view illustrating an assistive device.
Figure 10:
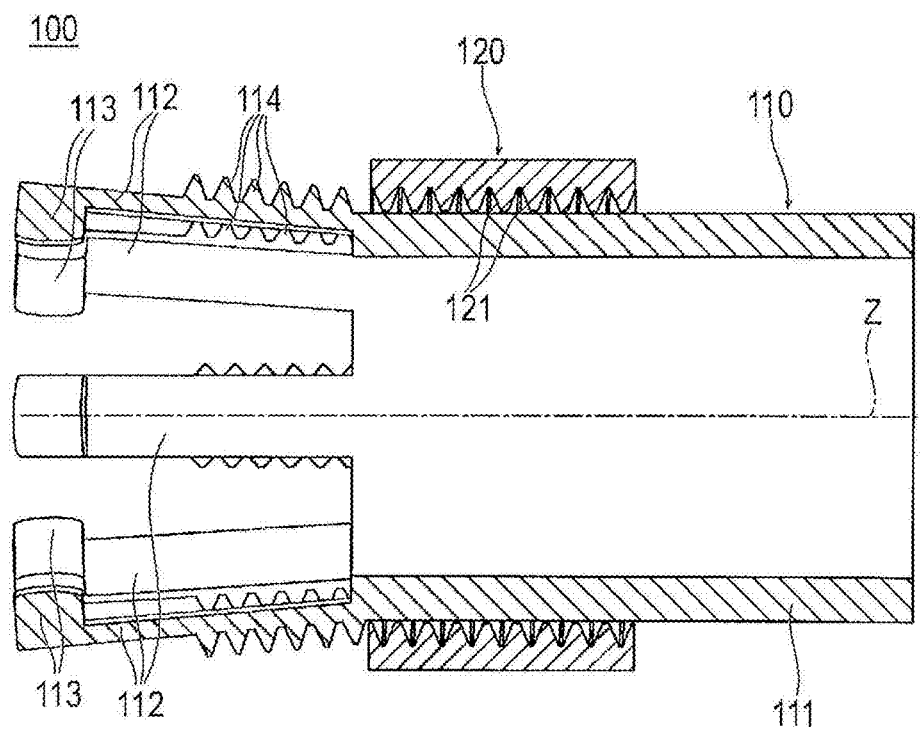
FIG. 10 is a longitudinal cross-sectional view illustrating the assistive device.

As illustrated in FIGS. 9 and 10, the assistive device 100 includes a tubular inner member 110 and a tubular outer member 120 which covers the outside of the inner member 110. The inner member 110 includes a tube-shaped circular tube portion 111 and a plurality of pressing portions 112 which project from and extend along an axial line (center axis) Z of the circular tube portion 111 from one side of an opening portion of the circular tube portion 111.

The inner diameter of the circular tube portion 111 is slightly greater than the outer diameter of the outer catheter proximal portion 41.

The pressing portions 112 arranged in the circumferential direction of the circular tube portion 111 are equal in number to the number of outer convex portions 82 and inner concave portions 78 (eight, in the embodiment disclosed by way of example). A pressing convex portion 113 protruding in an inward direction is provided on the inner circumferential surface side on the distal side or distal end (a side or end in the direction extending from the circular tube portion 111) in each of the pressing portions 112. The outer circumferential surface of the pressing portion 112 is obliquely shaped (i.e., is angled outwardly as shown in FIGS. 9 and 10) so as to cause the distal ends of the pressing portions 112 to open or spread outward. Screw threads 114 are formed on an outer surface of the pressing portions 112.

The outer member 120 is a circular tube-shaped member possessing an inner diameter substantially coinciding with (equal to) the outer diameter of the circular tube portion 111, and screw grooves 121 are formed on the inner surface of the outer member 120 so that the screw threads 114 on the inner member 111 spirally fit with or threadably engage the screw grooves 121 of the outer member 120.

Figure 11:
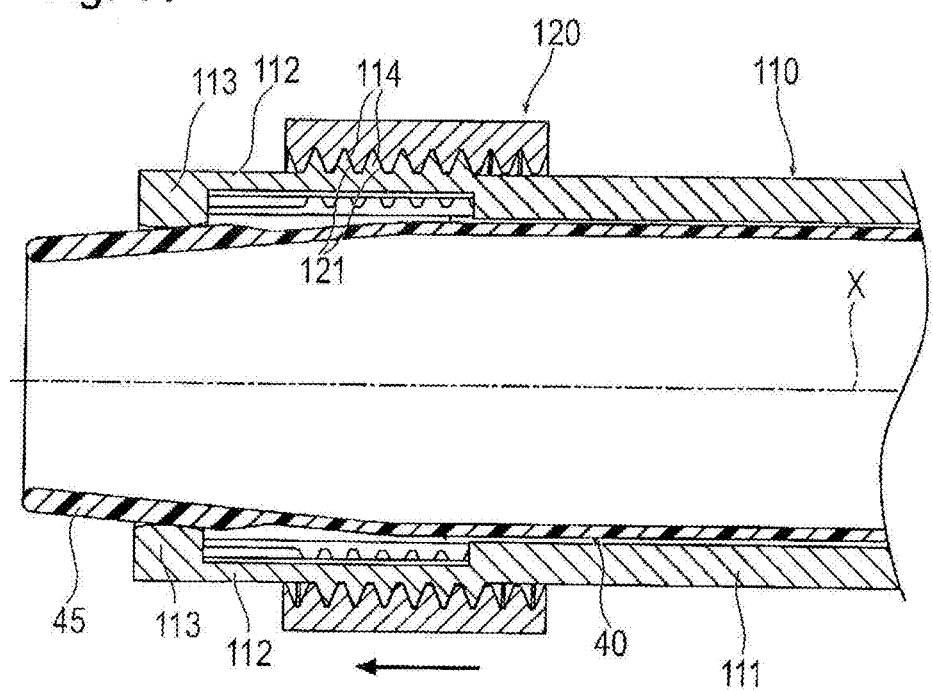
FIG. 11 is a longitudinal cross-sectional view illustrating a state where the outer catheter distal portion is decreased in diameter by the assistive device.

If the outer member 120 rotates in a state where the outer member 120 covers the circular tube portion 111, the screw threads 114 of the inner member 110 spirally engage the screw grooves 121 of the outer member 120 as illustrated in FIG. 11. Thus, the outer member 120 can be moved in the distal end direction, that is, a direction in which the pressing portions 112 are provided. If the outer member 120 moves in a direction toward the pressing portions 112, the obliquely formed pressing portions 112 receive a force from the outer member 120 and so the pressing portions 112 are deformed so as to be inclined in the inward direction.

Set forth next is an example of a method of using the catheter assembly 10 of the present embodiment.

Figure 12:
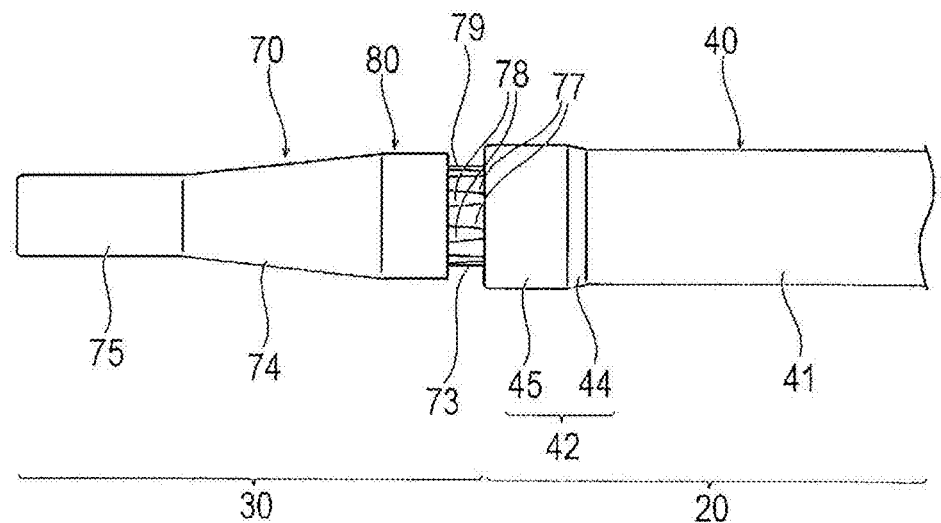
FIG. 12 is a plan view illustrating a state where an inner catheter body is inserted into an outer catheter body.
Figure 13:
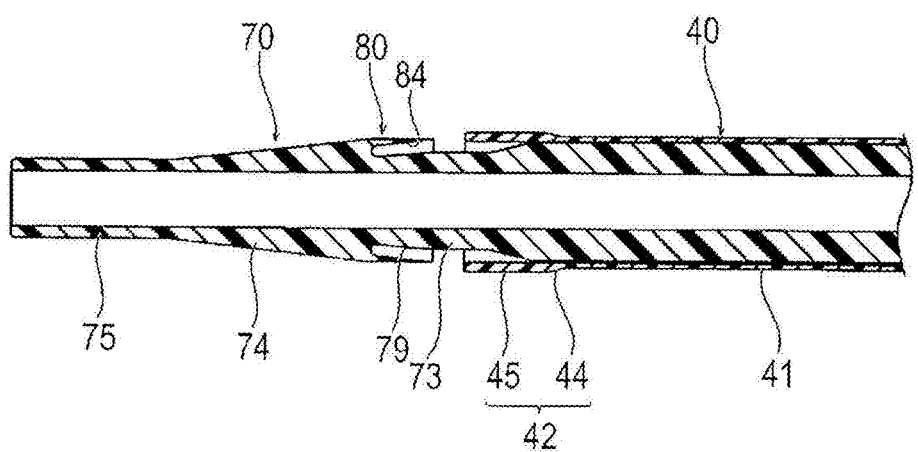
FIG. 13 is a cross-sectional view illustrating the state where the inner catheter body is inserted into the outer catheter body.

Firstly, before the catheter assembly 10 is introduced into a blood vessel, the outer catheter 20 and the inner catheter 30 are assembled, as illustrated in FIGS. 12 and 13. When assembling the outer catheter 20 and the inner catheter 30, the inner catheter distal portion 75 is inserted into the opening portion at the proximal end of the outer hub 50 in the outer catheter 20 and is thrust or moved forward, and then, the inner catheter 30 is advanced relative to the outer catheter 20 so that the second inner catheter decreasing diameter portion 74, the inner catheter distal portion 75, and the accommodation unit 80 reach a farther distal side than the outer catheter distal portion 45. That is, the inner catheter 30 is advanced relative to the outer catheter 20 so that the second inner catheter decreasing diameter portion 74, the inner catheter distal portion 75, and the accommodation unit 80 are positioned distally beyond the distal-most end of the outer catheter distal portion 45 as shown in FIG. 13. Subsequently, the outer catheter body 40 is covered with the assistive device 100 in a state where the outer member 120 is arranged outside the circular tube portion 111 in which the outer member 120 encircles or axially overlaps the circular tube portion 111 (refer to FIGS. 9 and 10), and the pressing portions 112 are positioned outside the outer catheter distal portion 45 in axial overlapping relation to the outer catheter distal portion 45. Then, the circular tube portion 111 is positioned on the proximal side of the pressing portions 112. Subsequently, the outer member 120 is rotated while maintaining the position of the inner member 110, and so the screw threads 114 of the inner member 110 threadably engage the screw grooves 121 of the outer member 120, as illustrated in FIG. 11. Thus, the outer member 120 moves in the distal end direction. If the outer member 120 moves in a direction of the pressing portions 112, the obliquely formed pressing portions 112 receive a force from the outer member 120 and are deformed so as to be inclined in the inward direction (i.e., pressed inwardly). Thus, the outer catheter distal portion 45 is deformed inwardly in the radial direction by the pressing portions 112. In this case, since the number of pressing portions 112 arranged in the circumferential direction of the circular tube portion 111 is the same as the number of the outer convex portions 82 and the inner concave portions 78, the outer catheter distal portion 45 is annularly and elastically deformed and possesses a wavy-shape in a cross section which is orthogonal to the axial line X of the outer catheter 20, thereby being decreased in diameter. That is, the outer catheter distal portion 45 is annularly and elastically deformed to take on a wavy cross-sectional shape like the wavy cross-sectional shape of the inner side accommodation surface 79 and the outer side accommodation surface 84. As the outer catheter distal portion 45 is annularly and inwardly deformed to flex and exhibit a wavy-shaped cross-section, the entirety of the outer catheter distal portion 45 in the circumferential direction can be uniformly and effectively decreased in diameter as much as possible.

Thereafter, while causing a portion which is inwardly deformed in the radial direction of the outer catheter distal portion 45 to face the inner concave portion 78 of the inner catheter small diameter portion 73, the outer catheter 20 is moved relatively in the distal end direction with respect to the inner catheter 30, as illustrated in FIGS. 14 to 16. Thus, the distal end or distal end portion of the outer catheter distal portion 45 is inserted into the accommodation space 81. In this case, the outer catheter distal portion 45 having the inner diameter greater than the outer diameter of the inner catheter body 70 is decreased in diameter in a natural state so that the outer catheter distal portion 45 can be accommodated inside the accommodation unit 80 of the inner catheter 30. Moreover, the first inner catheter decreasing diameter portion 72 and the inner catheter smaller diameter portion 73 are decreased in diameter in the distal end direction in a tapered manner, the heights of the inner convex portion 77 and the outer convex portion 82 gradually increase in the distal end direction, and the depths of the inner concave portion 78 and the outer concave portion 83 gradually deepen in the distal end direction. Thus, the distal end regions of the outer catheter distal portion 45, the tapered portion 44, and the outer catheter proximal portion 41 are smoothly deformed so as to be gradually decreased in diameter in the distal end direction.

Subsequently, the pressing portions 112 move outwardly in the radial direction by rotating the outer member 120 so as to move the outer member 120 in the proximal direction with respect to the inner member 110, thereby separating the pressing portions 112 from the outer catheter distal portion 45. Thereafter, the assistive device 100 is moved in the distal end direction with respect to the catheter assembly 10, thereby detaching the assistive device 100 from the catheter assembly 10. The state of the outer catheter distal portion 45 which is accommodated in the accommodation unit 80 and is elastically deformed so as to be decreased in diameter is maintained by the accommodation unit 80. Accordingly, assembly of the outer catheter 20 and the inner catheter 30 is completed. It is not necessary to use the assistive device 100 when assembling the outer catheter 20 and the inner catheter 30. The catheter assembly 10 may be provided to a user in a state where the outer catheter 20 and the inner catheter 30 are already assembled. Alternatively, the outer catheter 20 and the inner catheter 30 can be provided to users separately, and can then be assembled by the users.

Figure 17:
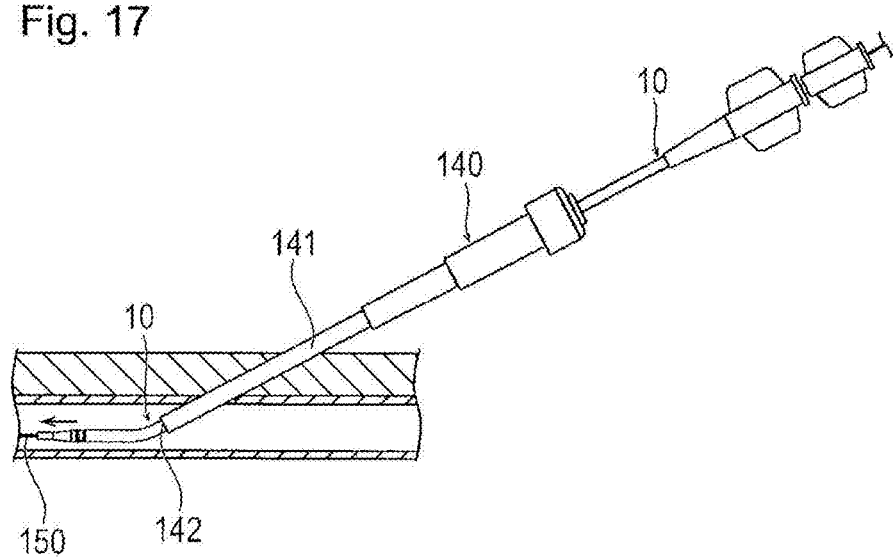
FIG. 17 is a cross-sectional view illustrating a state where the catheter assembly is inserted into a blood vessel.
Figure 18:
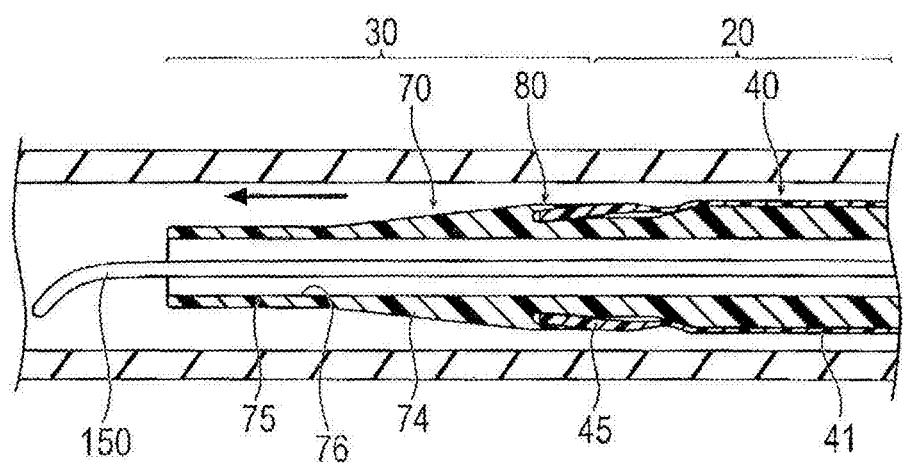
FIG. 18 is a cross-sectional view illustrating a state where the catheter assembly is thrust forward in a blood vessel.

Subsequently, as illustrated in FIGS. 17 and 18, the radial artery, the brachial artery, the femoral artery, or the like is punctured by a catheter introducer 140 according to the Seldinger's method. Then, the catheter assembly 10 in a state where a guide wire 150 is inserted into the lumen 76 is inserted into the catheter introducer 140. Thereafter, the guide wire 150 is caused to advance, and the distal end of the catheter assembly 10 is inserted into the artery from a distal opening 142 of a sheath 141. The insertion of the catheter assembly 10 into the artery is performed while checking positions and postures of the catheter assembly 10 under X-ray fluoroscopy. The portion for introducing is not particularly limited. That is, the insertion of the catheter assembly 10 into the artery can be performed under X-ray fluoroscopy to confirm the position and direction of the catheter assembly 10. The portion for introducing is also not limited to the aforementioned arteries. For example, the blood vessel into which the catheter assembly 10 is inserted not limited to arteries (the radial artery, the brachial artery, the femoral artery), as the catheter assembly 10 is also applicable to (can be inserted into) other blood vessels (e.g. veins).

Subsequently, while causing the guide wire 150 to advance, the catheter assembly 10 is gradually thrust forward to a target site. In this case, since the catheter assembly 10 has a double structure in which the inner catheter 30 and the outer catheter 20 axial overlap one another, collapse is unlikely to occur compared to a single structure catheter yet it is possible to maintain the thickness of the outer catheter body 40 to be relatively thin and the inner diameter to be maximized. Therefore, the catheter assembly 10 is unlikely to be warped resulting in an improvement of kink resistance. The catheter assembly 10 is unlikely to be warped when passing through a bent blood vessel as well. Rigidity of the catheter assembly is enhanced due to the double structure. Therefore, a hand force is easily transferred to the distal end, and unnecessary bending of the catheter assembly 10 during introduction to a target site can be prevented. Since the inner catheter body 70 is inserted into the outer catheter body 40, the catheter assembly 10 assembled with the outer catheter 20 and the inner catheter 30 exhibits appropriate rigidity, and thus, it is possible to straighten a bent blood vessel to some extent so as to rather easily pass through the blood vessel. Since the relatively thin outer catheter distal portion 45 is accommodated in the accommodation unit 80, the distal end of the relatively thin outer catheter distal portion 45 can move inside a blood vessel without coming into contact with the blood vessel. Therefore, a blood vessel can be prevented from being damaged, and the outer catheter distal portion 45 can be prevented from being turned inside out due to resistance applied to the distal end from a blood vessel. Since the outer catheter distal portion 45 is decreased in diameter and is accommodated in the accommodation unit 80 of the inner catheter 30, a step difference generated between the inner catheter 30 and the outer catheter 20, that is, a step difference generated between the outer circumferential surface of the accommodation unit 80 and the outer catheter distal portion 45 can be smoothed. Thus, a blood vessel can be prevented from being damaged due to the step difference. Since the first inner catheter decreasing diameter portion 72 and the inner catheter smaller diameter portion 73 are decreased in outer diameter in the distal end direction in a tapered manner, the distal end regions of the outer catheter distal portion 45, the tapered portion 44, and the outer catheter proximal portion 41 can be deformed so as to be gradually decreased in diameter in the distal end direction, smoothness on the outer circumferential surface of the outer catheter body 40 is maintained. Thus, loads to a blood vessel during insertion into the blood vessel can be reduced. Since the second inner catheter decreasing diameter portion 74 is provided at the distal end of the inner catheter 30, loads to a blood vessel applied by the distal end of the inner catheter 30 can be reduced and the catheter assembly 10 can relatively smoothly move inside the blood vessel.

Figure 19:
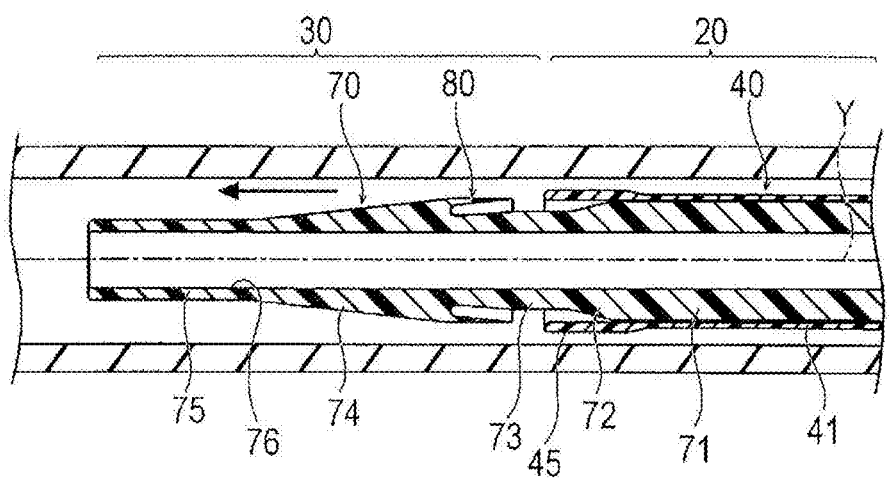
FIG. 19 is a cross-sectional view illustrating a state where the outer catheter distal portion is separated from the accommodation unit.

After the distal end of the catheter assembly 10 reaches a target site, as illustrated in FIG. 19, the guide wire 150 is removed out from the lumen 76 of the inner catheter 30. Then, the inner catheter 30 is moved in the distal end direction with respect to the outer catheter 20, or the outer catheter 20 is moved in the proximal direction with respect to the inner catheter 30. Thereafter, the outer catheter distal portion 45 which is decreased in outer diameter and is accommodated in the accommodation unit 80 is moved in the proximal direction with respect to the accommodation unit 80, thereby being separated from the accommodation unit 80. As the outer catheter distal portion 45 is separated from the accommodation unit 80, the outer catheter distal portion 45 expands in outer diameter so as to be restored to its former shape (the original shape of the catheter distal portion 45 before the outer catheter distal portion 45 is placed in the accommodation unit 80), that is, a shape before being deformed in waves on account of its own restoring force (elasticity). The minimum inner diameter of the outer catheter distal portion 45 having the expanded diameter coinciding with the outer catheter distal portion 45 in the axial line Y direction is equal to or greater than the maximum outer diameter of a portion (in the present embodiment, the distal portion of the inner catheter proximal portion 71, the first inner catheter decreasing diameter portion 72, the inner catheter smaller diameter portion 73, the second inner catheter decreasing diameter portion 74, the inner catheter distal portion 75, and the accommodation unit 80) of the inner catheter 30 which can be positioned on a farther distal side than the outer catheter distal portion 45. That is, when the outer catheter distal portion 45 expands in its original shape, the minimum inner diameter of the outer catheter distal portion 45 is equal to or greater than the maximum outer diameter of a portion of the inner catheter 30 which is positionable distally of the distal end of the outer catheter distal portion 45. The outer catheter distal portion 45 has an equal diameter along the axial line X (i.e., the diameter of the outer catheter proximal portion 41) of the outer catheter before accommodation in the accommodation unit 80 as illustrated in FIG. 4. Therefore, the inner diameter of the outer catheter distal portion 45 can probably be restored to the same diameter of the outer catheter proximal portion 41 when the outer catheter distal portion 45 is released from the accommodation unit 80. However, the outer catheter distal portion 45 may not be restored to its original shape perfectly since the outer catheter distal portion 45 is deformed and decreased in outer diameter during accommodation in the accommodation unit. Even in such a case, it is possible to remove the inner catheter from the lumen 43 of the outer catheter 20 if the minimum inner diameter of the outer catheter distal portion 45 is greater than the maximum outer diameter of a portion of the inner catheter 30 which can be positioned on a farther distal side than (distally of) the outer catheter distal portion 45. The outer catheter distal portion 45 is not necessarily restorable to the former natural state in a perfect shape, and slight deformation may remain.

Figure 20:
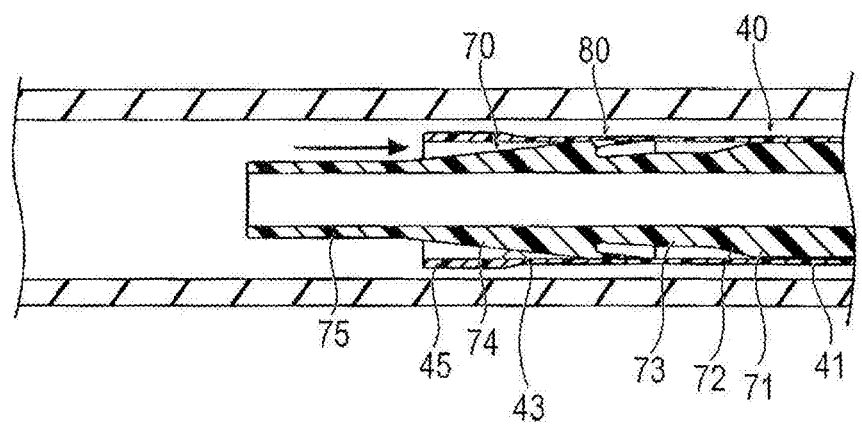
FIG. 20 is a cross-sectional view illustrating a state where the inner catheter is drawn out from the outer catheter.

Subsequently, as illustrated in FIG. 20, while causing the outer catheter 20 to remain (i.e., the outer catheter 20 is held or maintained stationary), the inner catheter 30 is moved in the proximal direction, and then, the inner catheter 30 is completely removed from the lumen 43 of the outer catheter 20. In this case, since the minimum inner diameter of the outer catheter distal portion 45 having the expanded diameter coincides with the outer catheter distal portion 45 in the axial line Y direction or is equal to or greater than the maximum outer diameter of a portion of the inner catheter 30 which can be positioned on a farther distal side than the outer catheter distal portion 45, the portion of the inner catheter 30 can easily pass through the inside of the outer catheter distal portion 45. In the outer catheter 20 after the inner catheter 30 is removed, since the outer catheter distal portion 45 is thin in thickness, but is still thicker than that of the outer catheter proximal portion 41, and is formed of a soft material, damage to a blood vessel can be minimized.

Thereafter, long instruments (linear objects) such as catheters (for example, a PTCA balloon catheter), an endoscope, an ultrasonic probe, and a temperature sensor can be inserted or removed, or various types of liquid such as a contrast agent (an X-ray contrast agent), a drug solution, and saline can be injected or discharged through the outer hub 50 of the outer catheter 20 and the lumen 43 of the outer catheter body 40. After completing medical treatment performed through the outer catheter 20, the outer catheter 20 is removed from the catheter introducer 140, and the catheter introducer 140 is removed from the blood vessel (artery), thereby completing a practice.

As described above, the catheter assembly 10 according to the present embodiment includes the outer catheter 20 that has the tubular outer catheter body 40, and the inner catheter 30 (the shaft) that has the inner catheter body 70 (the shaft body) which is insertable into the outer catheter body 40. The inner catheter 30 has an accommodation unit 80 which extends in the proximal direction from the inner catheter body 70, can be positioned on a farther distal side than the outer catheter body 40 in a state where the inner catheter body 70 is inserted into the outer catheter body 40, and can accommodate the outer catheter distal portion 45 so as to surround the outer circumference of the outer catheter distal portion 45 in a state where the outer catheter distal portion 45 formed at the distal end of the outer catheter body 40 is reduced in diameter. The outer catheter distal portion 45 can be separated from the accommodation unit 80 and can expand in diameter by relatively moving the inner catheter body 70 in the distal end direction with respect to the outer catheter body 40 from a state of being accommodated in the accommodation unit 80. Therefore, in the catheter assembly 10, the outer catheter distal portion 45 is accommodated in the accommodation unit 80, and thus, it is possible to prevent damage to a blood vessel without allowing the distal end of catheter distal portion 45 to come into contact with the blood vessel when moving inside the blood vessel. The outer catheter distal portion 45 is decreased in diameter and is accommodated in the accommodation unit 80 of the inner catheter 30 so that a step difference generated between the inner catheter 30 and the outer catheter 20 can be smoothed. Thus, a blood vessel can be prevented from being damaged due to the step difference. The inner space of the outer catheter body 40 can be widely maintained and the inner catheter body 70 can be arranged to be movable inside the outer catheter body 40 due to the expanded diameter of the outer catheter body 40, and thus, the inner catheter body 70 can be easily removed from the outer catheter body 40. A medical instrument or liquid such as medicine and a contrast agent can favorably pass through the lumen 43 of the outer catheter body 40 due to the expanded diameter of the outer catheter body 40.

Since the outer catheter distal portion 45 has the thickness in the radial direction greater than that of the proximal portion of the outer catheter body 40, sharpness of the distal end of the outer catheter distal portion 45 can be minimized, and damage to a blood vessel can be minimized.

Since the minimum inner diameter of the outer catheter distal portion 45 in a state where the outer catheter distal portion 45 is separated from the accommodation unit 80 and expands in diameter coinciding with the outer catheter distal portion 45 in the axial line X direction is equal to or greater than the maximum outer diameter of a portion of the inner catheter 30 which can be positioned on a farther distal side than the outer catheter distal portion 45, a portion which needs to pass through the inside of the outer catheter distal portion 45 easily passes through the inside of the outer catheter distal portion 45.

Since in a state where the outer catheter distal portion 45 is accommodated in the accommodation unit 80, at least one (both in the present embodiment) of the outer side accommodation surface 84 of the accommodation unit 80 facing the outer circumferential surface of the outer catheter distal portion 45 and the inner side accommodation surface 79 of the accommodation unit 80 facing the inner circumferential surface of the outer catheter distal portion 45 is deformed into an annular wavy-shaped cross section orthogonal to the axial line Y of the inner catheter body 70, the outer catheter distal portion 45 can be accommodated in the accommodation unit 80 while effectively maintaining a state of flexing to possesses a wavy-shaped cross-section and being decreased in diameter.

If the outer catheter distal portion 45 is accommodated in the accommodation unit 80 so that the outer catheter distal portion 45 is decreased in diameter, a user can omit the operation that involves positioning the outer catheter distal portion 45 in the accommodation unit 80, and thus, workability is improved. That is, the catheter assembly 10 can be provided to users (e.g. medical doctor) before the outer catheter 20 and the inner catheter 30 are assembled by the manufacturer or after the outer catheter 20 and the inner catheter 30 are assembled by the manufacturer. It is more useful for users when the outer catheter 20 and the inner catheter 30 are already assembled because the user can use the catheter assembly immediately without the need for assembling.

Figure 21:
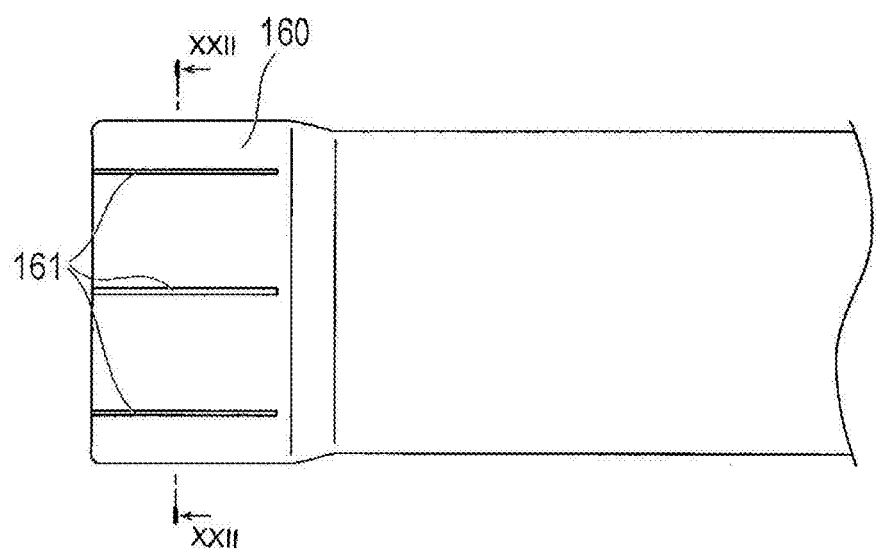
FIG. 21 is a plan view illustrating a modification example of the outer catheter.
Figure 22:
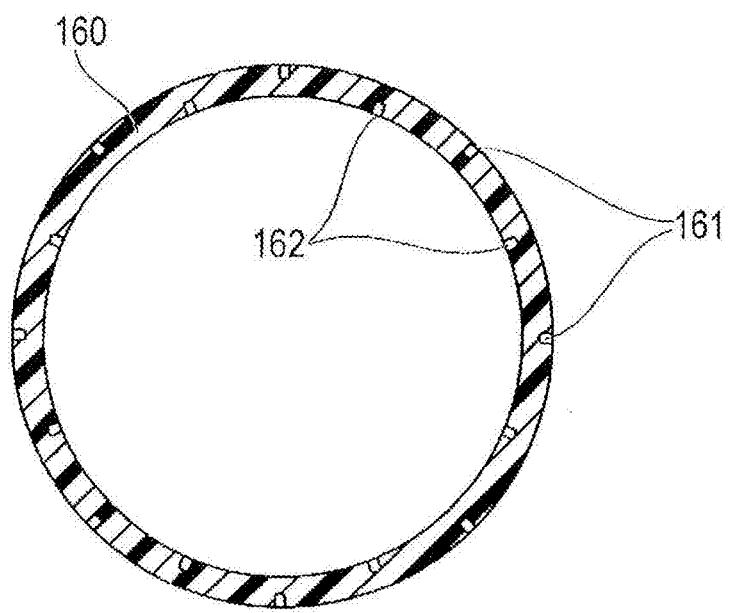
FIG. 22 is a transverse cross-sectional view taken along the section line XXII-XXII in FIG. 21.
Figure 23:
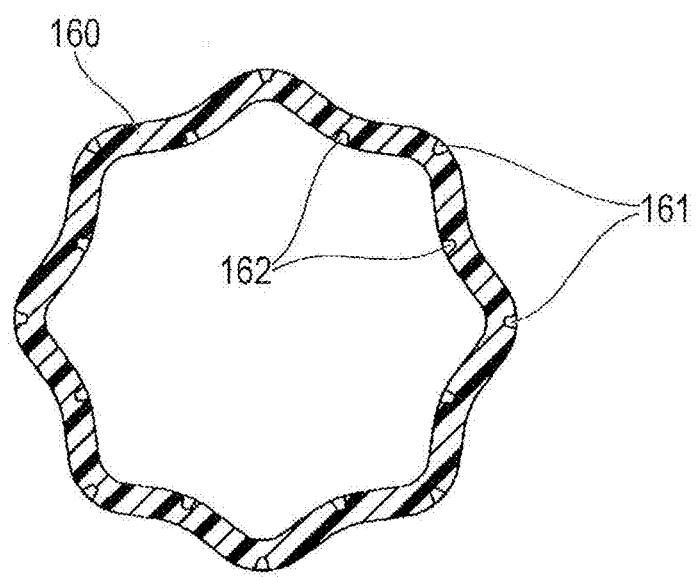
FIG. 23 is a transverse cross-sectional view illustrating a state where the outer catheter distal portion of the outer catheter according to the modification example is decreased in diameter.

The present invention is not limited to only the above-described embodiment. Various modifications and changes can be made by those skilled in the art within the technical scope of the present invention. For example, in one modified example illustrated in FIGS. 21 and 22, an outer catheter distal portion 160 may partially include outer fragile portions 161 (fragile portions) and inner fragile portions 162 (fragile portions) which are low in rigidity. The outer fragile portions 161 are grooves extending in an axial direction (parallel to the central axis of the outer catheter distal portion 160) on the outer circumferential surface of the outer catheter distal portion 160. In the illustrated embodiment disclosed by way of example, eight grooves are formed at equivalent intervals in the circumferential direction. The inner fragile portions 162 are grooves extending in the axial direction (parallel to the central axis of the outer catheter distal portion 160) on the inner circumferential surface of the outer catheter distal portion 160. In the illustrated embodiment disclosed by way of example, eight grooves are formed at equivalent intervals in the circumferential direction so that each of the grooves forming the inner fragile portions 162 is positioned circumferentially between a pair of the grooves forming the outer fragile portions 161. A portion provided with the outer fragile portion 161 is relatively easily deformed so as to have a convex outer surface, and a portion provided with the inner fragile portion 162 is relatively easily deformed so as to have a convex inner surface. Therefore, a particular portion of the outer catheter distal portion 160 can be caused to rather easily bend in a particular direction by providing the inner fragile portions 162 and the outer fragile portions 161 in the outer catheter distal portion 160. Thus, as illustrated in FIG. 23, the outer catheter distal portion 160 can be rather easily decreased in diameter. Only one of the outer fragile portion 161 and the inner fragile portion 162 may be provided in the outer catheter distal portion 160. The form of the fragile portion is not limited to a grooved form. For example, a material forming the fragile portion may be partially changed.

At least one of the outer catheter body and the inner catheter body may be configured to be curved. At least one of the outer catheter body and the inner catheter body may be configured to have a multi-layer, and a reinforcement layer formed with a linear object or a braided object may be provided.

The outer catheter distal portion may have the same thickness in the radial direction as that of the outer catheter proximal portion. The outer catheter distal portion may be formed of the same material as that of the outer catheter proximal portion.

Both the outer side accommodation surface and the inner side accommodation surface in the inner catheter do not have to be annularly formed while being flexural in waves on a cross section which is orthogonal to the axial line Y of the inner catheter body as long as the outer catheter distal portion decreased in diameter can be accommodated.

Usage of the catheter assembly is not particularly limited as long as the catheter assembly is used by being inserted into a biological lumen. Therefore, for example, the outer catheter may be a catheter introducer, and the inner catheter (the shaft) may be a dilator. For example, a biological lumen may be a vas, the ureter, the bile duct, the oviduct, and the hepatic duct without being limited to a blood vessel. The shaft which is inserted into the outer catheter may be a solid member in place of a tubular body.

The detailed description above describes a catheter assembly. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:
1. A catheter assembly comprising:
an outer catheter comprised of a tubular outer catheter body, the outer catheter body possessing a distal end portion terminating at a distal-most end of the outer catheter body, the distal end portion of the outer catheter body possessing an outer circumferential surface;
a shaft comprised of a shaft body insertable into the outer catheter body;
the shaft including an accommodation unit extending in a proximal direction from the shaft body in axial overlying and spaced apart relation to an outer circumferential surface of a portion of the shaft body so that a gap exists between the accommodation unit and the portion of the shaft body defining an accommodation space that is configured to receive the distal end portion of the outer catheter body; and
the distal end portion of the outer catheter body being separable from the accommodation unit by relatively moving the shaft body in a distal end direction with respect to the outer catheter body from a state of being accommodated in the accommodation unit so that the outer diameter of the distal end portion of the outer catheter body expands upon being separated from the accommodation unit;
wherein the distal end portion of the outer catheter body possesses a thickness in a radial direction thicker than the thickness of a portion of the outer catheter body proximal of the distal end portion.

2. The catheter assembly according to claim 1, wherein a minimum inner diameter of the distal end portion of the outer catheter body in a state where the distal end portion of the outer catheter body is separated from the accommodation unit is equal to or greater than a maximum outer diameter of a portion of the shaft which is positionable distally of the distal-most end of the outer catheter body.

3. The catheter assembly according to claim 2, wherein
in a state where the distal end portion of the outer catheter body is accommodated in the accommodation unit, at least one of an outer side accommodation surface of the accommodation unit facing the outer circumferential surface of the distal end portion of the outer catheter body and an inner side accommodation surface of the accommodation unit facing an inner circumferential surface of the distal end portion of the outer catheter body is annular, possesses a wavy-shape in a cross-section orthogonal to an axis of the shaft body and flexes when a force is applied.

4. The catheter assembly according to claim 3, wherein the distal end portion of the outer catheter body partially includes a plurality of fragile portions which are lower in rigidity than an adjoining portion of the distal end portion of the outer catheter body that is devoid of the fragile portions, the fragile portions being spaced apart from one another in a circumferential direction.

5. The catheter assembly according to claim 1, wherein the distal end portion of the outer catheter body partially includes a plurality of fragile portions which are lower in rigidity than an adjoining portion of the distal end portion of the outer catheter body that is devoid of the fragile portions, the fragile portions being spaced apart from one another in a circumferential direction.

6. A catheter assembly positionable in a blood vessel of a living body, the catheter assembly comprising:
an outer catheter configured to be positioned in the blood vessel in the living body, the outer catheter comprising a tubular outer catheter body possessing a distal end portion terminating at a distal-most end of the outer catheter body, the distal end portion of the outer catheter body possessing an outer diameter as well as inner and outer circumferential surfaces;
a shaft comprised of a tubular shaft body open at opposite ends and possessing a distal-most end and a proximal-most end;
the shaft including an accommodation unit positioned so that a portion of the shaft body extends distally beyond a distal-most end of the accommodation unit and a portion of the shaft body extends proximally beyond a proximal-most end of the accommodation unit, the accommodation unit extending in a proximal direction from the shaft body in axial overlying and spaced apart relation to an outer circumferential surface of a portion of the shaft body so that a gap exists between the accommodation unit and the portion of the shaft body defining an accommodation space that is configured to receive the distal end portion of the outer catheter body;
the shaft being configured to be positioned in the outer catheter, the shaft and the outer catheter being relatively movable such that the shaft and the outer catheter body are positionable in a first state in which the distal end portion of the outer catheter body is positioned in the accommodation space with the accommodation unit overlying and contacting the distal end portion of the outer catheter body to reduce the outer diameter of the distal end portion of the outer catheter body and are positionable in a second state in which the distal end portion of the outer catheter body is removed from the accommodation space to expand the outer diameter of the distal end portion of the outer catheter body;
wherein the distal end portion of the outer catheter body possesses an inner circumferential surface and an outer circumferential surface, the inner circumferential surface of the distal end portion of the outer catheter body being wavy-shaped around the entire circumference of the inner circumferential surface of the distal end portion.

7. The catheter assembly according to claim 6, wherein the outer circumferential surface of the distal end portion of the outer catheter body is wavy-shaped around the entire circumference of the outer circumferential surface of the distal end portion.

8. The catheter assembly according to claim 6, wherein the distal end portion of the outer catheter body possesses an inner circumferential surface and an outer circumferential surface, the outer circumferential surface of the distal end portion of the outer catheter body being wavy-shaped around the entire circumference of the outer circumferential surface of the distal end portion.

9. The catheter assembly according to claim 6, wherein the accommodation unit possesses an inner side accommodation surface facing the inner circumferential surface of the distal end portion of the outer catheter body, the inner side accommodation surface of the accommodation unit being wavy-shaped around the entire circumference of the inner side accommodation surface of the accommodation unit.

10. The catheter assembly according to claim 6, wherein the distal end portion of the outer catheter body possesses a thickness in a radial direction that is greater than the thickness of a portion of the outer catheter body proximal of the distal end portion of the outer catheter body.

11. The catheter assembly according to claim 6, wherein the shaft body includes: a proximal portion possessing a distal end; a decreasing diameter portion possessing distal and proximal ends, and an outer diameter that is smaller at the distal end of the decreasing diameter portion than at the proximal end of the decreasing diameter portion; and a smaller diameter portion possessing an outer diameter smaller than the outer diameter of the proximal portion; the decreasing diameter portion extending in a distal direction from the distal end of the proximal portion; the smaller diameter portion extending in the distal direction from the distal end of the decreasing diameter portion, the accommodation unit axially overlying the smaller diameter portion.

12. The catheter assembly according to claim 11, wherein the decreasing diameter portion is a first decreasing diameter portion, the shaft body further including a second decreasing diameter portion possessing proximal and distal ends, the second decreasing diameter portion extending distally from a distal end of the smaller diameter portion, the second decreasing diameter portion possessing an outer diameter that is smaller at the distal end of the second decreasing diameter portion than at the proximal end of the second decreasing diameter portion.

* * * * *